United States Patent
Micheyl

(10) Patent No.: US 11,419,526 B2
(45) Date of Patent: Aug. 23, 2022

(54) METHOD AND APPARATUS FOR CHARACTERIZING TINNITUS USING BAYESIAN MINIMUM-ENTROPY PSYCHOMETRIC PROCEDURE

(71) Applicant: Starkey Laboratories, Inc., Eden Prairie, MN (US)

(72) Inventor: Christophe D. Micheyl, Millery (FR)

(73) Assignee: Starkey Laboratories, Inc., Eden Prairie, MN (US)

( * ) Notice: Subject to any disclaimer, the term of this patent is extended or adjusted under 35 U.S.C. 154(b) by 1485 days.

(21) Appl. No.: 14/858,991

(22) Filed: Sep. 18, 2015

(65) Prior Publication Data

US 2016/0089061 A1    Mar. 31, 2016

Related U.S. Application Data

(60) Provisional application No. 62/056,966, filed on Sep. 29, 2014.

(51) Int. Cl.
  *A61B 5/12* (2006.01)
  *A61B 5/00* (2006.01)

(52) U.S. Cl.
  CPC .............. *A61B 5/128* (2013.01); *A61B 5/123* (2013.01); *A61B 5/6815* (2013.01); *A61B 5/6898* (2013.01); *A61B 5/72* (2013.01)

(58) Field of Classification Search
  CPC ........... A61B 5/128; A61B 5/123; A61B 5/72; A61B 5/6898; A61B 5/6815
  See application file for complete search history.

(56) References Cited

U.S. PATENT DOCUMENTS

| | | | |
|---|---|---|---|
| 8,014,870 B2 | 9/2011 | Seidman | |
| 8,088,077 B2 | 1/2012 | Turner et al. | |
| 8,353,846 B2 | 1/2013 | Henry et al. | |
| 9,795,325 B1 * | 10/2017 | Merzenich | A61B 5/123 |
| 2006/0036297 A1 * | 2/2006 | Seidman | A61N 1/361 607/55 |
| 2010/0008526 A1 * | 1/2010 | De Vries | H04R 25/70 381/314 |

(Continued)

FOREIGN PATENT DOCUMENTS

| | | |
|---|---|---|
| WO | WO-0242986 A1 | 5/2002 |
| WO | WO-2007042043 A2 | 4/2007 |

OTHER PUBLICATIONS

Basile, Charles-Édouard, et al., "Psychoacoustic Assessment to Improve Tinnitus Diagnosis", PLoS One. 8(12): e82995, (14 pgs), Dec. 12, 2013.

(Continued)

*Primary Examiner* — Rene T Towa
(74) *Attorney, Agent, or Firm* — Schwegman Lundberg & Woessner, P.A.

(57) ABSTRACT

A system for measuring tinnitus of a patient using a Bayesian minimum-entropy psychometric procedure for which a probabilistic model of the patient's behavior is combined with an optimal statistical-inference method to generate a test sound to be presented to the patient. The test sound includes a sequence of sound components selected and arranged to facilitate, expedite, and improve the reliability of tinnitus measurements.

20 Claims, 2 Drawing Sheets

(56) References Cited

U.S. PATENT DOCUMENTS

2013/0163797 A1* 6/2013 Suzman .............. H04R 25/50
                                                    381/314
2013/0338527 A1   12/2013 Suh et al.

OTHER PUBLICATIONS

Henry, James A., "Psychoacoustic Measures of Tinnitus", J Am Acad Audiol 11(2000), (2000), 138-155.

Norena, AJ, "Psychoacoustic characterization of the tinnitus spectrum: implications for the underlying mechanisms of tinnitus", Audiol Neurootol 7, (2002), 358-369.

Tyler, RS, et al., "Tinnitus pitch: a comparison of three measurement methods", Br J Audiol. 17(2), (1983), 101-107.

* cited by examiner

US 11,419,526 B2

METHOD AND APPARATUS FOR CHARACTERIZING TINNITUS USING BAYESIAN MINIMUM-ENTROPY PSYCHOMETRIC PROCEDURE

CLAIM OF PRIORITY

The present application claims the benefit of priority under 35 U.S.C. § 119(e) of U.S. Provisional Patent Application Ser. No. 62/056,966, filed on Sep. 29, 2014, which application is incorporated herein by reference in its entirety.

TECHNICAL FIELD

This document relates generally to audio systems and more particularly to a system for characterizing tinnitus with test sound generated using a Bayesian minimum-entropy psychometric procedure.

BACKGROUND

Tinnitus is a condition in which a patient perceives a sound in the ears in absence of a corresponding external sound. While ringing in the ears is associated with tinnitus, other types of sounds can be perceived and can be sporadic, intermittent or continuous. Tinnitus can be caused by various conditions or injuries, but regardless of cause can be debilitating and decrease a patient's quality of life.

Because tinnitus has different causes and symptoms, and different patients may perceive different sounds in the ears, its diagnosis includes characterizing the tinnitus for each individual patient. As part of a diagnostic procedure, for example, a clinician may play various sounds to a patient complaining about tinnitus, and the patient identifies the sound that most closely matches his or her tinnitus. Subsequently, treatment may be determined for the patient based on the identified characteristics (such as frequencies) of the tinnitus.

SUMMARY

A system for measuring tinnitus of a patient using a Bayesian minimum-entropy psychometric procedure for which a probabilistic model of the patient's behavior is combined with an optimal statistical-inference method to generate a test sound to be presented to the patient. The test sound includes a sequence of sound components selected and arranged to facilitate, expedite, and improve the reliability of tinnitus measurements.

In one embodiment, the system includes a sound generation device and a sound delivery device. The sound generation device includes a processing circuit that selects parameters for a test sound using a minimum-entropy probabilistic model of the patient's behavior in conjunction with a Bayesian-inference method and a paired-comparison psychometric procedure, and produces an output sound signal representing the test sound using the selected parameters. The sound delivery device produces the test sound based on the output sound signal and delivers the sound to the ears of the patient.

In one embodiment, a method for testing a patient is provided. Parameters for a test sound are selected using a minimum-entropy probabilistic model of the patient's behavior in conjunction with a Bayesian-inference method and a paired-comparison psychometric procedure. An output sound signal representing the test sound is produced using the selected parameters.

This Summary is an overview of some of the teachings of the present application and not intended to be an exclusive or exhaustive treatment of the present subject matter. Further details about the present subject matter are found in the detailed description and appended claims. The scope of the present invention is defined by the appended claims and their legal equivalents.

DETAILED DESCRIPTION

Figure 1:
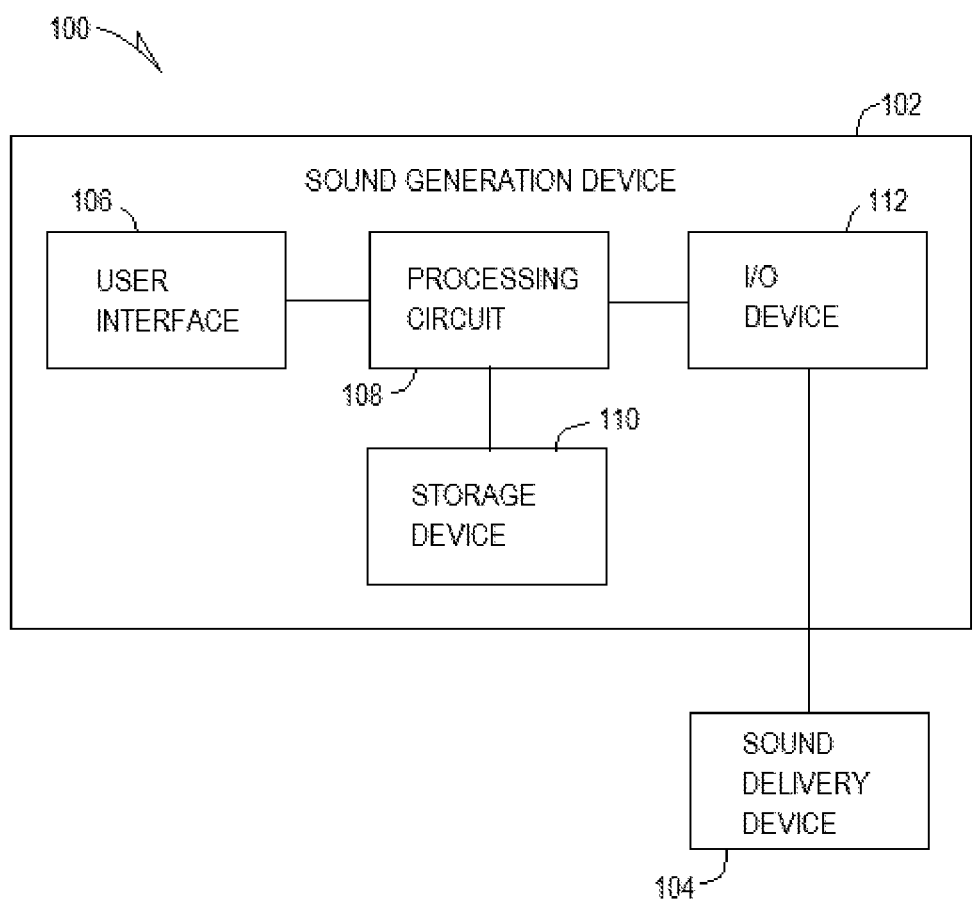
FIG. 1 is a block diagram illustrating an embodiment of a system for tinnitus measurement.

The following detailed description of the present subject matter refers to subject matter in the accompanying drawings which show, by way of illustration, specific aspects and embodiments in which the present subject matter may be practiced. These embodiments are described in sufficient detail to enable those skilled in the art to practice the present subject matter. References to "an", "one", or "various" embodiments in this disclosure are not necessarily to the same embodiment, and such references contemplate more than one embodiment. The following detailed description is demonstrative and not to be taken in a limiting sense. The scope of the present subject matter is defined by the appended claims, along with the full scope of legal equivalents to which such claims are entitled.

This document discusses, among other things, a system for characterizing tinnitus with a test sound generated using a Bayesian minimum-entropy psychometric procedure. To measure tinnitus for a patient, a clinician may present a test sound including a variety of sound components to that patient. The sound components may include sounds of different types (tones, narrowband noises, wideband noises, etc.) and/or different frequencies. Significant factors affecting efficiency and reliability of such a tinnitus measurement relate to the choice of psychometric procedure for stimulus presentation. Choice of the sound components and order of their presentation to the patient need to be determined for prompt yet accurate characterization of tinnitus. In this document, a "test sound" includes a sequence of sounds (referred to as sound components or stimuli) presented to the test subject (patient) during a tinnitus measurement session. In other words, a "tinnitus measurement session" includes the presentation of a test sound, i.e., a sequence of sound components (stimuli) to the patient.

In an example of a system for tinnitus measurement, the clinician or the patient manually (using a slider for example) adjusts the parameters (such as frequency and volume) of the test sound along a continuum until a match to the tinnitus is obtained. This method does not easily lend itself to automation. In addition, with this measurement method, it is difficult to ensure that the space of possible stimulus values is explored adequately and efficiently; thus, the quality of the measurement depends critically on the thoroughness and precision of the operator (the clinician or the patient), and consequently it is difficult to ascertain confidence in test results. In another example of a system for tinnitus measurement, stimuli from a predetermined set (e.g., a series of tones at different frequencies) are presented sequentially (one after the other) to the patient either in a predetermined order or in a random order, and the patient judges all of them. This constant-stimuli method can be automated, but it is highly inefficient. It is slow and tedious for both the clinician and the patient. In yet another example of a system for tinnitus measurement, sounds are presented sequentially to the patient, whose task is to indicate whether the sound is higher/lower than the tinnitus. A deterministic (decision tree) procedure is then used, whereby the relevant stimulus parameter (frequency or intensity) is increased or decreased depending on the patient's response to progressively narrow the range around the tinnitus parameter of interest (pitch or loudness). This bracketing method can be automated, but is relatively inefficient; therefore, with this method, clinicians and patients may have to spend an unnecessarily long time to arrive at a desired level of measurement accuracy. In addition, pitch matching via bracketing depends on the patient's ability to make relative pitch judgments (higher' or 'lower') in comparing the stimulus to the tinnitus, which many patients find difficult to do reliably.

The present subject matter relates a new psychometric procedure that combines a probabilistic model of the patient's behavior with an optimal statistical-inference method (Bayesian minimum-entropy) to facilitate, speed-up, and improve the reliability of tinnitus measurements. The present system uses prior information to improve tinnitus measurements, such as by expediting and/or increasing the accuracy of the tinnitus measurements. As more data concerning tinnitus characteristics in relation to other audiometric variables (e.g., the audiogram) become available, this advantageous feature of the present system becomes even more apparent and significant. In various embodiments, the present system allows tinnitus measurement to be performed more efficiently than the other systems discussed above. Use of the Bayesian optimal-design principles allows the present system to easily modify selection of parameters for the test sound to take advantage of prior information when such information is available, which is impossible with the other systems discussed above.

In various embodiments, the present system selects the parameters (e.g., frequency) of the test sound to be presented to the patient on the next trial (i.e., parameters defining the next sound component or next set of sound components in the sequence) in order to ensure efficient (fast yet accurate) measurement of tinnitus. This is accomplished by using a minimum-entropy algorithm in conjunction with a Bayesian-inference method and a paired-comparison psychometric procedure to obtain optimally-efficient measurements of perceptual characteristics of tinnitus (e.g., pitch). The paired-comparison psychometric procedure includes presenting the sound components in pairs to the patient, and the patient identifies the one of the sound components closer to his or her tinnitus. The presentation of each pair of sound components (stimuli) may be referred to as a trial. For example, "the next trial" includes delivering the next pair of sound components (stimuli) in the sequence to the patient.

An advantage of the present system is its high efficiency. In the context of the present system, an efficient measurement procedure means: a procedure which uses few steps to reach a pre-determined accuracy or, a procedure which yields a high level of accuracy after a pre-determined number of steps. The efficient measurement procedure as discussed in this document has the potential to produce faster and/or more accurate measurements than any other existing procedures in measuring tinnitus. Another advantage of the present system is that, in addition to estimates of tinnitus characteristics, it provides a measure of confidence in test results. This confidence measure is being computed throughout the test, making it possible for the clinician to make a cogent decision as to when the measurement can be stopped, at any time during the test. Yet another advantage of the present systems is that it incorporates prior information to further improve measurement accuracy and/or measurement speed. In various embodiments, useful prior information may include data found in relevant scientific literature, data previously collected from the same patient, and/or data previously collected from other tinnitus patients. Such prior information may be stored in a database to be used by the present system.

While the application in tinnitus measurement is discussed as a specific example, the present subject matter generally provides for a new psychometric procedure that combines a probabilistic model of the patient's behavior with an optimal statistical-inference method (Bayesian minimum-entropy) to facilitate, speed-up, and improve the reliability of any test that use a test sound for matching a sound perceived by the subject being tested.

FIG. 1 is a block diagram illustrating an embodiment of a system 100 for tinnitus measurement. System 100 includes a sound generation device 102 and a sound delivery device 104. In various embodiments, system 100 may be used by a user such as a clinician who evaluates a patient complaining about tinnitus or the patient who evaluates his or her own tinnitus.

Sound generation device 102 includes a user interface 106, a processing circuit 108, a storage device 110, and an input/output (I/O) device 112. User interface 106 presents information to the user and receives commands and other information from the user, such as information identifying the patient and testing commands and results for the patient. Processing circuit 108 produces an output sound signal representing a test sound to be used in a tinnitus measurement procedure that is customized for the patient, by using prior information related to the patient's condition. In various embodiments, processing circuit 108 is configured to select parameters (e.g., frequency) of the test sound using a minimum-entropy algorithm in conjunction with a Bayesian-inference method and a paired-comparison psychometric procedure to obtain optimally-efficient measurements of perceptual characteristics of tinnitus (in particular, pitch). The paired-comparison psychometric procedure includes presenting sound components to the patient in pairs, and the patient is to indicate which sound component of the pair of sound components is closer to his or her tinnitus. The test sound is to be presented to the patient in a way that ensures efficient (fast yet accurate) measurement of tinnitus. Storage device 110 stores various information used by processing circuit 108 in the synthesis of the test sound, such as useful prior information previously collected from the patient being tested, other tinnitus patients, and/or relevant scientific literature. I/O device 112 includes one or more input and/or output ports to allow sound generation device to receive information such as the prior information used in the synthesis of the test sound, and delivers the output sound signal to sound delivery device 104. The output sound signal is a time-domain electrical signal representing the test sound. In one embodiment, sound generation device 102 communicates with sound delivery device 104 via a wired link through which the output sound signal is transmitted. In another embodiment, sound generation device 102 communicates with sound delivery device 104 via a wireless link through which the output sound signal is transmitted.

Sound delivery device 104 produces the test sound based on the output sound signal and delivers to sound to the ears of the patient. In various embodiments, sound delivery device 104 can include any acoustic transducer that is capable of converting the output sound signal to the test sound. In one embodiment, sound delivery device 104 includes a headphone (set of earphones). In another embodiment, sound delivery device 104 includes a pair of hearing aids. In another embodiment, sound delivery device 104 includes one or more speakers. In one embodiment, sound delivery device 104 delivers the test sound to the patient in a soundproof room during the tinnitus measurement. In another embodiment, sound delivery device 104 delivers the test sound to the patient in any suitable environments, including the patient's home, during the psychoacoustic evaluation of tinnitus.

In various embodiments, the circuit of each device discussed in this document is implemented using hardware, software, firmware or a combination of hardware, software and/or firmware. In various embodiments, processing circuit 108 may be implemented using one or more circuits specifically constructed to perform one or more functions discussed in this document or one or more general-purpose circuits programmed to perform such one or more functions. Examples of such general-purpose circuit can include a microprocessor or a portion thereof, a microcontroller or portions thereof, and a programmable logic circuit or a portion thereof.

Figure 2:
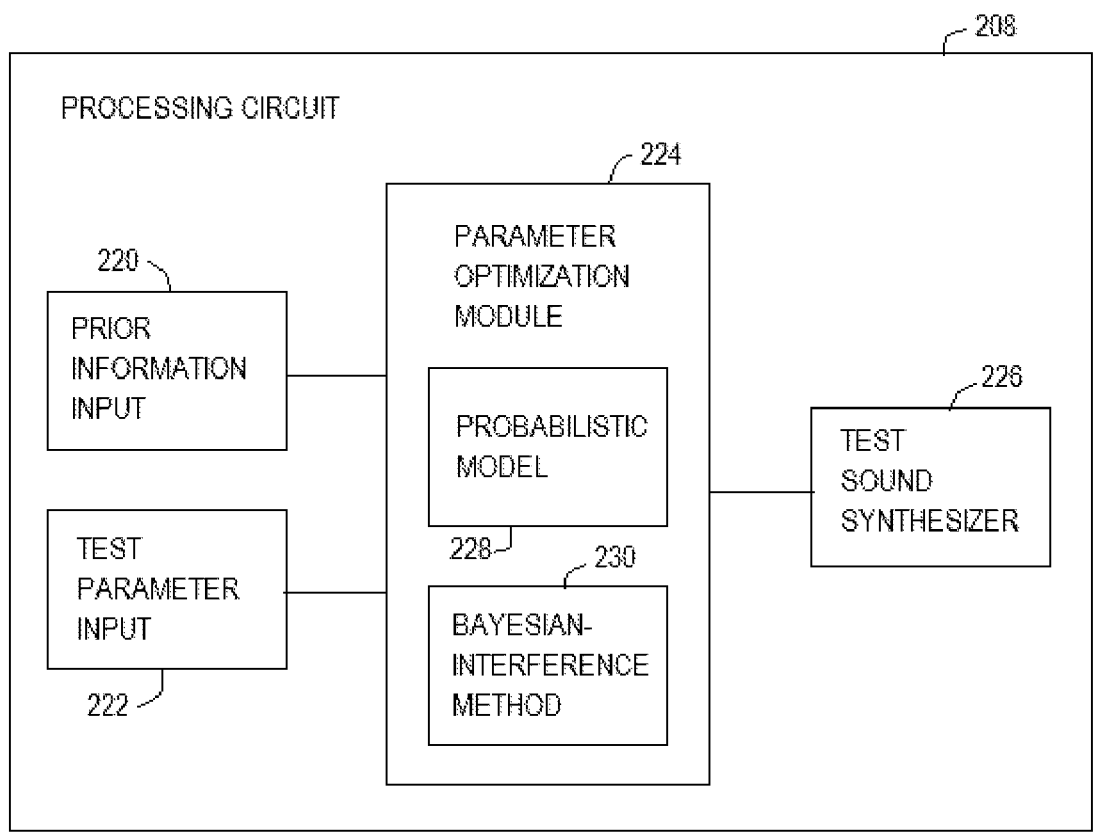
FIG. 2 is a block diagram illustrating an embodiment of a processing circuit of the system for tinnitus measurement.

FIG. 2 is a block diagram illustrating an embodiment of a processing circuit 208, which represents an embodiment of processing circuit 108. Processing circuit 208 includes a prior information input 220, a test parameter input 222, a parameter optimization module 224, and a test sound synthesizer 226. Prior information input 220 receives the prior information used in the parameter selection, such as from storage device 110 or I/O device 112. In various embodiments, the prior information received by prior information input may include data previously collected from the patient being tested (which may include data resulting from trials already occurred in the same tinnitus measurement session), data collected from other tinnitus patients, and/or information found in relevant scientific literature. Test parameter input 222 receives test-sound parameters, such as from storage device 110 or user interface 106. Examples of test-sound parameters include center frequency, target loudness or target sound level, sound type or timbre, and left/right balance. Parameter optimization module 224 selects parameters for the test sound from the received test-sound parameters using the received prior information for an approximately optimally efficient tinnitus measurement, as further discussed below. Test sound synthesizer 226 produces the output sound signal, which is a time-domain electrical signal representing the test sound, based on the parameters selected by parameter optimization module 224.

In various embodiments, parameter optimization module 224 selects parameters for the test sound using a probabilistic model 228 in conjunction with a Bayesian-inference method 230 and a paired-comparison psychometric procedure. Probabilistic model 228 is a minimum-entropy probabilistic model of the patient's behavior established based the prior information used in the parameter selection. In various embodiments, parameter optimization module 224 approximately optimally selects parameters for the pair of sound components of the test sound used for the next trial of an adaptive two-alternative force-choice tinnitus-measurement procedure, in such a way that the tinnitus measurement is likely to be approximately optimally efficient. The tinnitus measurement is considered to be optimally efficient when the estimation accuracy is the highest for a predetermined number of steps, or when the number of steps required for a predetermined level of estimation accuracy is the smallest. The steps may include the number of trials required in the tinnitus measurement, i.e., the number of sound components (stimuli) in the test sound. In order to achieve the maximal efficiency, the sound components (stimuli) presented to the patient on the next trial is to be chosen in such a way that the information gained concerning one or more tinnitus characteristics being measured is maximized. In other words, the next pair of sound components (stimuli) should be selected so that, after they have been presented to the patient and a response has been obtained, the one or more tinnitus characteristics of interest are estimated as precisely as possible, or equivalently, the uncertainty of these estimates is as low as possible, given the prior information available up to this point.

Such an optimization procedure mathematically corresponds to minimizing the expected entropy of the posterior distribution of a parameter of interest (a tinnitus characteristic in the present subject matter, for example pitch), or a vector of parameters, over the stimulus set. Denoting as θ the parameter (or vector of parameters) being estimated, as s the vector of stimulus parameters, and as r the response of the subject to these stimuli, the posterior distribution of θ given r is given by Bayes theorem:

$$P(\theta \mid r, s) = \frac{P(r \mid \theta, s) p(\theta, s)}{p(r.s)}.$$

By definition, the stimulus- and response-conditional entropy of the posterior is:

$$h(r,s) = +\int P(\theta|r,a) \ln(P(\theta|r,s)) d\theta.$$

The expected posterior entropy (with the expectation taken over r) is:

$$E_r[h(r, s)] = \sum_r P(r \mid s) h(r, s).$$

The stimulus parameters are selected using:

$$S = \arg\min_s E_r[h(r,s)].$$

To apply the general minimum-entropy principle in the context of tinnitus measurement, a probabilistic model of the sensory and decisional processes leading from the presentation of a stimulus pair $s = \{s_1, s_2\}$ to the generation of a response by the patient under test, as to which of the two stimuli most resembles his/her tinnitus, are formulated.

In one embodiment of this model, the probability that the patient identifies stimulus $s_1$ as resembling the tinnitus more than stimulus $s_2$ is computed as:

$$P(r = 1 \mid \mu, s) = \int_0^{+\infty} \frac{1}{\sqrt{2\pi}\sigma} e^{-\frac{1}{2}\left(\frac{z - [f(\frac{s_1 - \mu}{\omega}) - f(\frac{s_2 - \mu}{\omega})]}{\sigma}\right)^2} dz.$$

where the function $f(.)$, also known as the patient's 'likeness' function, is a monotonically decreasing function of the absolute value of its argument, $\mu$, $\omega$, and $\sigma$ are model parameters corresponding to the patient's tinnitus frequency, the width (or length-scale) of the patient's likeness function ($f$), and the internal noise (a measure of the patient's unreliability or response-inconsistency), respectively. In various other embodiments, the function $f(.)$ is a periodic function of its argument, with the period corresponding to one octave so as to simulate octave errors.

Posterior distributions and maximum-a-posteriori (MAP) estimates of the parameters can be estimated using deterministic or sampling-based computational Bayesian inference methods. In one embodiment, Gibbs sampling is used to approximate the joint posterior distribution of the parameters based on conditional marginals. In another embodiment, posteriors are computed on a grid.

Posterior distributions and MAP estimates can be used to compute a measure of confidence in test results. In one embodiment, the confidence measure is taken to be the reciprocal of the entropy of the posterior distribution of the tinnitus-frequency parameter, $\mu$.

System 100 has been implemented in a prototype and evaluated. Results from six test subjects each being a patient with tinnitus confirmed that the present system is fast (a few minutes only for the measurement of tinnitus pitch), easy for the patient, and yields generally reproducible results (good test-retest variability). In the prototype, processing circuit 208 is configured using Matlab® code implementing one example of a procedure for measuring the pitch of tinnitus. The code is provided, by way of example and not by way of restriction, in the Appendix below.

In various embodiments, system 100 can be configured for use by clinicians who perform the psychoacoustic evaluation of tinnitus, and/or configured for automating tinnitus measurement directly by the end-user (patients). In various embodiments, sound generation device 102 may be implemented as a dedicated device or in another device such as a desktop computer, laptop computer, tablet computer, or smartphone.

In various embodiments, sound delivery device 104 can be any device capable of producing the test sound using the output sound signal produced by sound generation device 102. Examples of such device include, but are not limited to, headphone, earphones, ear buds, and hearing aids. Examples of such hearing aids include, but are not limited to, behind-the-ear (BTE), in-the-ear (ITE), in-the-canal (ITC), receiver-in-canal (RIC), or completely-in-the-canal (CIC) type hearing aids. It is understood that behind-the-ear type hearing aids may include devices that reside substantially behind the ear or over the ear. Such devices may include hearing aids with receivers associated with the electronics portion of the behind-the-ear device, or hearing aids of the type having receivers in the ear canal of the user, including but not limited to receiver-in-canal (RIC) or receiver-in-the-ear (RITE) designs. The present subject matter can also be used with hearing assistance devices generally, such as cochlear implant type hearing devices. It is understood that other hearing assistance devices not expressly stated herein may be used in conjunction with the present subject matter.

This application is intended to cover adaptations or variations of the present subject matter. It is to be understood that the above description is intended to be illustrative, and not restrictive. The scope of the present subject matter should be determined with reference to the appended claims, along with the full scope of legal equivalents to which such claims are entitled.

This application is intended to cover adaptations or variations of the present subject matter. It is to be understood that the above description is intended to be illustrative, and not restrictive. The scope of the present subject matter should be determined with reference to the appended claims, along with the full scope of legal equivalents to which such claims are entitled.

What is claimed is:

1. A system for testing a patient having tinnitus, comprising:
a sound generation device including:
a processing circuit configured to:
produce an output sound signal using parameters, the output sound signal representing a test sound including a sequence of sound components to be presented in pairs of sound components to the patient, the pairs of sound components each to be used in a trial of multiple trials during a paired-comparison psychometric procedure of a tinnitus measurement session, the parameters defining each pair of the pairs of sound components; and
determine the parameters during the tinnitus measurement session using a probabilistic model of the patient's behavior established using prior information for minimizing an expected entropy of a posterior distribution of a tinnitus-characterizing parameter or vector of tinnitus-characterizing parameters according to a Bayesian-inference method, the prior information including data related to the patient's condition collected prior to the tinnitus measurement session and portions of responses by the patient to the multiple trials that have been received for one or more trials of the multiple trials having already occurred during the tinnitus measurement session, the responses by the patient identifying a sound component from each of the pairs of sound components that more closely resembles the tinnitus in each trial of the multiple trials;
a user interface configured to receive the responses by the patient to the multiple trials; and
an input/output device configured to receive the prior information; and a sound delivery device configured to produce the test sound using the output sound signal and to deliver the produced test sound to the patient.

2. The system of claim 1, wherein the processing circuit is configured to select a frequency of the parameters for the test sound.

3. The system of claim 2, wherein the sound generation device further comprises a storage device storing the data related to the patient's condition.

4. The system of claim 2, wherein the sound generation device further comprises an input/output device configured to receive the data related to the patient's condition.

5. The system of claim 1, wherein the sound delivery device is communicatively coupled to the sound generation device via a wireless link.

6. The system of claim 1, wherein the sound delivery device comprises hearing aids.

7. The system of claim 1, wherein the sound delivery device comprises a headphone.

8. The system of claim 1, wherein the sound delivery device comprises ear buds.

9. A system for measurement of tinnitus for a patient, comprising:
a processing circuit including: a prior information input configured to receive prior information;
a test parameter input configured to receive test-sound parameters;
a parameter optimization module configured to select parameters for a test sound from the received test-sound parameters, the test sound including a sequence of sound components to be presented in pairs of sound components to the patient, the pairs of sound components each to be used in a trial of multiple trials during a paired-comparison psychometric procedure of a tinnitus measurement session, the parameter optimization module configured to select during the tinnitus measurement session parameters defining each pair of the pairs of sound components using a probabilistic model of the patient's behavior established using the received prior information for minimizing an expected entropy of a posterior distribution of a tinnitus-characterizing parameter or vector of tinnitus-characterizing parameters according to a Bayesian-inference method, the received prior information including data collected from the patient prior to the tinnitus measurement session and portions of responses by the patient to the multiple trials that have been received for one or more trials of the multiple trials having already occurred during the tinnitus measurement session, the responses by the patient identifying a sound component from each of the pairs of sound components that more closely resembles the tinnitus in each trial of the multiple trials; and a test sound synthesizer configured to produce an output sound signal representing the test sound based on the selected parameters for the test sound;

a sound delivery device configured to produce the test sound based on the output sound signal and to deliver the produced test sound to the patient; and a user interface configured to receive the responses by the patient to the multiple trials.

10. The system of claim 9, wherein the processing circuit is configured to select a frequency of the parameters for the test sound.

11. The system of claim 10, wherein the sound delivery device comprises hearing aids.

12. A method for testing a patient having tinnitus, comprising:

producing an output sound signal using a processing circuit, the output sound signal representing a test sound using parameters, the test sound including a sequence of sound components presented in pairs of sound components to the patient, the pairs of sound components each to be used in a trial of multiple trials during a paired-comparison psychometric procedure of a tinnitus measurement session, the parameters defining each pair of the pairs of sound components;

determining the parameters during the tinnitus measurement session using a probabilistic model of the patient's behavior established using prior information for minimizing an expected entropy of a posterior distribution of a tinnitus-characterizing parameter or vector of tinnitus-characterizing parameters according to a Bayesian-inference method, the prior information including data related to the patient's condition collected prior to the tinnitus measurement session and portions of responses by the patient to the multiple trials that have been received for one or more trials of the multiple trials having already occurred during the tinnitus measurement session, the responses by the patient identifying a sound component from each of the pairs of sound components that more closely resembles the tinnitus in each trial of the multiple trials;

producing the test sound using the output sound signal using an acoustic transducer;

delivering the test sound to the patient during the tinnitus measurement session;

receiving the responses by the patients to the multiple trials using a user interface; and characterizing the tinnitus by receiving from the patient an identification of the sound component most closely resembling the tinnitus from the delivered test sound.

13. The method of claim 12, comprising receiving the data related to the patient's condition from the patient.

14. The method of claim 13, wherein selecting the parameters for the test sound comprises selecting the parameters for the test sound for minimizing a number of steps required for a predetermined level of estimation accuracy in the measurement of tinnitus.

15. The method of claim 13, wherein selecting the parameters for the test sound comprises selecting the parameters for the test sound for maximizing estimation accuracy for a predetermined number of steps in the measurement of tinnitus.

16. The method of claim 13, wherein the test-sound parameters comprise a frequency of the test sound.

17. The method of claim 13, further comprising using hearing aids to produce the test sound using the output sound signal and deliver the test sound to the patient.

18. The method of claim 13, further comprising using a headphone to produce the test sound using the output sound signal and deliver the test sound to the patient.

19. The method of claim 13, further comprising delivering the test sound to the patient in a soundproof room.

20. The method of claim 13, further comprising receiving the data related to the patient's condition collected from other patients.

* * * * *